United States Patent [19]

DelPesco

[11] 4,031,106

[45] June 21, 1977

[54] SYNTHESIS OF AROMATIC AMINES BY REACTION OF AROMATIC COMPOUNDS WITH AMMONIA

[75] Inventor: Thomas Wayne DelPesco, Wilmington, Del.

[73] Assignee: E. I. Du Pont de Nemours and Company, Wilmington, Del.

[22] Filed: Oct. 16, 1975

[21] Appl. No.: 622,890

Related U.S. Application Data

[63] Continuation-in-part of Ser. No. 429,028, Dec. 19, 1973, abandoned.

[52] U.S. Cl. .................... 260/296 R; 252/466 R; 260/288 R; 260/290 P; 260/294.9; 260/295 AM; 260/465 R
[51] Int. Cl.$^2$ ...................................... C07D 213/73
[58] Field of Search ........... 260/296 R, 581, 288 R, 260/290 P, 294.9, 295 AM

[56] References Cited

UNITED STATES PATENTS

| 2,643,256 | 6/1953 | Marsh | 260/288 |
|---|---|---|---|
| 2,948,755 | 8/1960 | Schmerling | 260/581 |

FOREIGN PATENTS OR APPLICATIONS

| 553,988 | 3/1958 | Canada | 260/581 |
|---|---|---|---|

OTHER PUBLICATIONS

Zielinski et al., Roczniki Chemii, vol. 45, pp. 1701 to 1708 (1971).

Primary Examiner—John D. Randolph

[57] ABSTRACT

An improved process is provided for producing an aromatic amine from ammonia and an aromatic compound which comprises reacting the aromatic compound with ammonia at a temperature of from about 150° C. to about 500° C. and at a pressure of from about 10 to about 1000 atmospheres in the presence of a conditioned nickel/nickel oxide/zirconium oxide cataloreactant containing an oxide of lanthanum, samarium, holmium, europium, erbium, yttrium, praseodymium, neodymium, terbium, ytterbium, dysprosium or a mixture of any of them.

8 Claims, No Drawings

1

SYNTHESIS OF AROMATIC AMINES BY REACTION OF AROMATIC COMPOUNDS WITH AMMONIA

CROSS REFERENCE TO RELATED APPLICATION

This a continuation-in-part of copending application Ser. No. 429,028 filed Dec. 19, 1973 now abandoned.

BACKGROUND OF THE INVENTION

As is well known, arylamines have been made in a variety of ways including reduction of the corresponding nitro compound, reaction of a chloro compound with ammonia either alone or with catalysts such as copper salts, reaction of phenols with ammonia and zinc chloride at an elevated temperature and by the well-known Hofmann amide rearrangement with a hypohalite or halogen and a base. For some time, more direct methods of producing arylamines have been sought.

More recently, Canadian Pat. No. 553,988 issued on Mar. 4, 1958 to Thomas describes a one-step process for the production of aromatic amines. One embodiment comprises contacting a mixture of benzene, ammonia and oxygen in the vapor phase with a platinum catalyst maintained at a temperature of about 1000° C. In another embodiment, a mixture of benzene and ammonia is contacted in the vapor phase with a reducible metal oxide such as nickel oxide at a temperature of about 100° C to 1000° C. The benzene is directly converted to aniline as represented by the equation

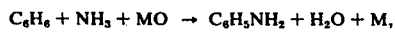

$$C_6H_6 + NH_3 + MO \rightarrow C_6H_5NH_2 + H_2O + M,$$

wherein M represents the metal and MO represents the oxide thereof.

U.S. Pat. No. 2,948,755 issued on Aug. 9, 1960 to Louis Schmerling describes the preparation of aromatic amines by reacting an aromatic compound such as benzene with anhydrous ammonia in the presence of a compound of a group VI-B metal such as molybdenum, tungsten or chromium and a promoter consisting of an easily reducible metallic oxide such as an oxide of copper, iron, nickel, silver or gold at a temperature in the range from about 200° to 600° C. The easily reducible metallic oxide is stated to perform as a hydrogen acceptor to thus remove the by-product hydrogen produced, causing the reaction to proceed in the desired direction.

An earlier reference, J. B. Wibaut, Berichte, 50, 541–6 (1917), reported the synthesis of aniline by passing benzene and ammonia through an iron tube packed with reduced nickel, iron, and asbestos at a temperature in the range of 550° to 600° C.

While the methods of these references do provide direct processes for the production of the aromatic amine, they do so in low conversions and yields of the aromatic compound to aromatic amine.

In an attempt to obviate these problems, it has been proposed to carry out the reaction betwen ammonia and the aromatic compound in the presence of a conditioned nickel/nickel oxide/zirconium oxide cataloreactant, so named because it acts as a catalyst as well as a reactant in the direct amination of an aromatic compound with ammonia. Prior to use in the reaction the cataloreactant is conditioned. That is, the nickel oxide component of the cataloreactant is partially reduced to elemental nickel in a reducing atmosphere such as hydrogen. The elemental nickel formed by this process is partially oxidized back to nickel oxide in an oxidizing atmosphere such as oxygen, air or water.

It has also been proposed to improve conversions obtained with the conditioned cataloreactant by ammonia treatment immediately before use in the reaction of the aromatic compound with ammonia. In spite of the improved results achieved using the conditioned cataloreactant as well as those which have been subjected to an ammonia treatment, the demands of production make it necessary to continue to search for improved systems which yield still higher conversion rates.

SUMMARY OF THE INVENTION

In accordance with this invention, it has been found that improved conversions of aromatic compounds to aromatic amines and longer cataloreactant life can be achieved when the aromatic compound is reacted with ammonia at a temperature of from about 150° C. to about 500° C. at a pressure of from about 10 to about 1000 atmospheres in the presence of a conditioned Ni/NiO/ZrO$_2$ cataloreactant containing an oxide of lanthanum, samarium, holmium, europium, erbium, praseodymium, neodymium, terbium, ytterbium, dysprosium, yttrium or mixtures thereof as a dopant. The cataloreactant containing one or more of the dopants of this invention may also be treated with ammonia immediately before use in the amination reaction.

The term dopant refers to an oxide of lanthanum, samarium, holmium, europium, erbium, praseodymium, neodymium, terbium, ytterbium, dysprosium, yttrium or mixtures thereof as an adjuvant which gives the cataloreactant composition of this invention its unique properties as more fully described hereinafter.

Thus in the process of the present invention, an aromatic compound selected from anthracene; phenanthrene; quinoline; isoquinoline and compounds having the formula $(X)_m(Y)_n$ wherein X is benzene or pyridine, $m$ is 1 or 2, $n$ is 0, 1 or 2, and Y is alkyl having one to six carbon atoms, halogen, nitrile, hydroxy, CONH$_2$, alkoxy having one to six carbon atoms, aryloxy, amino and aralkyl, with the proviso that when Y is aryloxy, a secondary or tertiary arylamine or an aralkyl, $n$ is 1 and when $n$ is 2, the substituents Y may be the same or different, is aminated by reacting ammonia with said aromatic compound at a temperature of from about 150° C. to about 500° C. and at a pressure of from about 10 to 1000 atmospheres, in the presence of a conditioned Ni/NiO/ZrO$_2$ cataloreactant with a mole ratio of nickel to nickel oxide of 0.001 to 10, the improvement has been found which comprises carrying out the reaction in intimate molecular contact with said conditioned cataloreactant containing a molar ratio of 0.0001 to 0.05 of a dopant to total nickel, wherein said dopant is selected from an oxide of lanthanum, samarium, holmium, europium, erbium, praseodymium, neodymium, terbium, ytterbium, dysprosium, yttrium and mixtures thereof.

DETAILED DESCRIPTION OF THE INVENTION

A. The Cataloreactant-Dopant System

The reaction between the aromatic compound and ammonia is an equilibrium reaction represented by the following equation using benzene as an example:

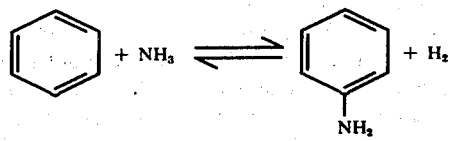

The mole ratio of ammonia/aromatic compound is preferably from 0.1 to 20, most preferably from 1.0 to 10, although any desired ratios may be employed.

The cataloreactants of the invention are nickel/nickel oxide/zirconium oxide compositions which function both as catalysts and as reactants in the amination of the aromatic compound. Specifically, the elemental nickel component catalyzes the reaction between the aromatic compound and ammonia while the nickel oxide component is the reactant. The nickel oxide is reduced to elemental nickel by the hydrogen formed during the reaction between the aromatic compound and ammonia. The zirconium oxide component is a support-promoter which enhances the catalytic properties of the cataloreactant and prevents reduced nickel crystallite coalescence by physically separating the crystallites. The preferred mole ratio of nickel to nickel oxide is from 0.001 to 10, most preferably from 0.01 to 1. The mole ratio of the total nickel in the form of nickel and nickel oxide in the cataloreactant to zirconium oxide expressed in terms of total nickel:zirconium is from 0.1 to 100, preferably from 0.3 to 20.

The cataloreactant of this invention is characterized by the fact that the size of the nickel crystallites varies from about 50 to 1000 A, preferably 80 to 250 A. If the crystallites are too large the activity of the cataloreactant is too low, and if the crystallites are too small unwanted side reactions take place because of overactivity.

The dopants of this invention are employed at a molar ratio of dopant to total nickel in the form of nickel and nickel oxide in the cataloreactant of from 0.0001 to 0.05. The use of the dopant increases the reactivity and prolongs the life of the cataloreactants of this invention. Such a result is entirely unexpected, particularly in view of the findings reported in a paper by Charcosset el al., published in the Journal of Catalysis, volume 22, pages 204–212, (1971) entitled "Increase of Reducibility of NiO by $H_2$, Due to Pretreatment with Salt Solutions" which states that lanthanum has no positive effect on the rate of reduction of NiO.

On the other hand, lanthanum oxide has been used with nickel oxide to improve the rate of carbon monoxide oxidation with oxygen to carbon dioxide as reported by Zielinski and Wachowski in an article in volume 45, of Roczniki Chemii (pages 1701–1709 ) entitled "Changes in the Physic-Chemical and Catalytic Properties of Lanthanum-Doped NiO".

In the oxidation reaction of Zielinski el al. the nickel oxide functions as a catalyst in contradistinction to the situation in the instant case in which the nickel oxide functions as a reactant. Therefore, the nickel oxide is not reduced to elemental nickel in the Zielinski et al. reaction. Indeed, the lanthanum oxide combines with the nickel oxide to yield a catalyst having a greater surface area and increased sintering resistance, both of which would enhance the apparent catalytic activity of the nickel oxide catalyst. While the applicant does not wish to be bound by any precise theory of operation, studies have shown that the phenomenon which occurs in the instant case arises because the lanthanum oxide (dopant) enters into the zirconium oxide lattice structure. There is no detectable effect of the addition of lanthanum oxide (dopant) on the nickel oxide phase as determined using standard phase analysis techniques.

The cataloreactant-dopant systems of this invention may be prepared by any suitable method. Generally, the system is precipitated from a solution of a nickel, zirconium and dopant compound such as the nitrate salt, by addition of a solution of a base such as ammonium carbonate, sodium hydroxide, lithium hydroxide, potassium hydroxide, ammonium hydroxide, sodium carbonate, sodium bicarbonate, potassium carbonate and the like and mixtures thereof. Additionally any nickel, zirconium and dopant-metal salt or ester which can react with an oxygen source, such as oxygen, water or part of the salt anion to give oxides or hydrous ozides can be used.

After the precipitation of the components of the cataloreactant-dopant system in the form of the oxide or hydrous oxide, the precipitate is filtered, washed, dried, reduced with hydrogen and exposed to a suitable amount of air or oxygen or optionally water until the desired oxidation product is achieved. The resulting solid product has a surface area of at least 1.35 square meters per gram, preferably 1.35 to 300 square meters per gram, most preferably 20 to 200 square meters per gram.

In the conditioning operation, the cataloreactant-dopant system is reduced by being exposed to hydrogen at a temperature between about 300° C. and 600° C., preferably 350° C. to 425° C. The $H_2$ pressure can vary from 0.1 atmosphere to 10 atmospheres and preferably 0.1 to 2 atmospheres of pressure are employed. From about 10 percent to 90 percent of the nickel oxide and preferably 25 percent to 60 percent is reduced to metallic nickel in this step. The cataloreactant-dopant is then oxidized by treatment with a gas containing from about 0.1 percent to about 21 percent of oxygen, preferably 1 percent to 5 percent, at 30° C. to 800° C., preferably 100° C. to 500° C., and at 0.1 atmosphere to 600 atmospheres, preferably 1 to 300 atmospheres pressure, preferably for the length of time necessary to achieve a Ni/NiO mole ratio of from 0.001 to 10, preferably from 0.01 to 1.

Following this intermediate reduction-oxidation or conditioning step the cataloreactant-dopant system may be subjected to an ammonia treatment immediately before use in the amination reaction. Ammonia treatment can be carried out in several ways. If a batch reactor is used for the subsequent amination reaction, the reactor can be charged with the cataloreactant-dopant system, sealed, pressurized with ammonia and heated or the reactor can first be heated under a blanket of nitrogen and then a stream of ammonia can be passed over the cataloreactant-dopant system before introducing the ammonia and aromatic compound.

In a continuous reactor, the ammonia can simply be passed through the conditioned system before the start of a new synthesis cycle. For the sake of expediency in either a batch or continuous operation, the ammonia treatment is carried out at the temperature to be used in the subsequent reaction between the ammonia and the aromatic compound. It is to be understood, however, that the ammonia pretreatment can be carried out effectively at from about room temperature (approximately 20° C.) to about 500° C. Preferably an elevated temperature is employed, most preferably between 250° C. and 400° C. The quantity of ammonia to total nickel in the nickel/nickel oxide components of the cataloreactant system expressed as part/part on a molar basis ranges from about 0.01 to 20.0 and preferably 0.1 to 2.0.

The duration of the ammonia pretreatment ranges from about 1 to about 60 minutes and preferably from about 3 to about 20 minutes.

Pure ammonia can be used in the pretreatment of the cataloreactant. Alternatively, the ammonia can be diluted with inert gases such as nitrogen or helium. Generally there is no advantage in diluting the ammonia.

B. The Amination

The conditions under which the reaction between ammonia and the aromatic compound is carried out depend somewhat on the particular reactants. In general, temperatures of from about 150° C. to about 500° C. and pressures of from about 10 atmospheres to about 1000 atmospheres will be employed.

The amination process may be carried out either batchwise or in a continuous operation. In a batch-type operation the cataloreactants of this invention are used in such quantities that the weight ratio of the cataloreactant to the aromatic compound is from 0.01 to 10, preferably from 0.2 to 3. Any suitable apparatus in which the reactants can be combined and mixed such as an agitated autoclave or a pressure vessel may be used as the reactor. Preferably, the reactor is heated to the reaction temperature before the amination reactants are introduced. Once the reactor contains the cataloreactant-dopant, ammonia and the aromatic compound to be aminated, it is sealed and the reaction is allowed to proceed to the degree of conversion desired. Thereafter, the apparatus and the contents are cooled to room temperature or lower, excess $NH_3$ pressure is vented and the aminated aromatic reaction product is separated from unreacted aromatic compounds, the cataloreactant-dopant and by-products by conventional means such as distillation, crystallization, and the like.

In a continuous operation, the process may be carried out in any suitable apparatus that will permit a contact time between the amination reactants and the cataloreactant-dopant system of from two seconds to twenty minutes, preferably 30 seconds to eight minutes. Some such suitable apparatus would include fixed bed reactors or packed vessels or coils, into which the cataloreactant-dopant, ammonia and the aromatic compound can be charged and the aromatic compound and ammonia can be passed through a cataloreactant-dopant bed. A moving bed operation may also be employed in which the reaction bed and the reactants either pass cocurrently or countercurrently to each other. Still another type of continuous operation which may be employed is a fluidized bed or slurry type in which the cataloreactant-dopant composition is carried into the reactor as a slurry in one or more of the reactants.

In either the batch or continuous type of reactor the aromatic compound and the ammonia may be introduced separately or as a single mixed stream. The cataloreactant may either be regenerated intermittently or continuously with oxygen or an oxygen containing gas such as air optionally with water. If desired the aromatic compound and ammonia may be reacted in the presence of water.

In the preferred embodiment of this invention, the amination reaction is carried out at a temperature in the range of about 250° C. to about 500° C. and at a pressure ranging from about 30 atmospheres to about 700 atmospheres.

Any aromatic compound with which ammonia is miscible at the temperature and pressure of the reaction and which comes into intimate molecular contact with the cataloreactant-dopant system of this invention may be directly aminated with ammonia as described herein. By intimate molecular contact is meant that, at the reaction temperature and pressure, the molecules of each reactant are in contact, on a molecular basis, with the cataloreactant-dopant system of this invention. The aromatic compounds of this invention are selected from benzene, naphthalene, anthracene, phenanthrene, pyridine, quinoline, isoquinoline, mono or di substituted counterparts of any of them and compounds of the general formula $(X)_m(Y)_n$ wherein X is benzene or pyridine, $m$ is 1 or 2, $n$ is 0, 1 or 2, and Y is selected from the group consisting of alkyl having one to six carbon atoms, halogen, nitrile, hydroxy, $CONH_2$, alkoxy having one to six carbon atoms, aryloxy, amino and aralkyl with the proviso that when Y is aryloxy, a secondary or tertiary arylamine or an aralkyl, $n$ is 1 and when $n$ is 2, the substituent Y may be the same or different.

The preferred aromatic compounds of the present invention are selected from anthracene, phenanthrene, quinoline, isoquinoline and compounds of the formula $(X)_m(Y)_n$ wherein X is selected from benzene and pyridine, $m$ is 1 or 2, $n$ is 0, 1 or 2 and Y is selected from alkyl having one to six carbon atoms, halogen, nitrile, hydroxy, $CONH_2$, alkoxy having one to six carbon atoms, aryloxy, amino and aralkyl with the proviso that when Y is selected from aryloxy, a secondary or tertiary arylamine, and aralkyl, $n$ is 1 and when $n$ is 2 the substituent Y may be the same or different. The most preferred aromatic compounds of this invention are selected from the group consisting of benzene, toluene, pyridine and aniline.

In the definition of aromatic compounds of the above-general formula, representative examples of alkyl having one to six carbon atoms include methyl, ethyl, propyl, butyl, amyl and hexyl, including cycloalkyl such as cyclohexyl and cyclopentyl. Representative examples of halogen include fluoro and chloro. Representative examples of alkoxy having one to six carbon atoms include methoxy, ethoxy, propoxy, butoxy, and hexoxy including cycloalkoxy such as cyclohexoxy and cyclopentoxy. A representative example of aryloxy includes phenoxy. Representative examples of amino include primary, secondary and tertiary amino wherein the secondary amino groups contain alkyl having one to five carbon atoms or aryl such as phenyl. Representative examples of aralkyl include benzyl, including mono and dialkyl substituted aralkyls, wherein the alkyl groups contain one to five carbon atoms such as 2-methylbenzyl, 3-ethylbenzyl, 2,3-dimethylbenzyl and the like. Any of the substituents of Y described herein may be contained on the naphthalene, anthracene, phenanthrene, quinoline and isoquinoline nucleus.

Additional representative examples of the aromatic compounds of the present invention include biphenyl, bipyridine, 4,4'-dichlorobiphenyl, toluene, o, m and p-xylene, aniline, chlorobenzene, fluorobenzene, 1,4-dichlorobenzene, ethylbenzene, anisole, 3-chloropyridine, 4-propylpyridine, hexylbenzene, 4-ethoxypyridine, phenoxy benzene, 4-phenoxypyridine, 3-aminopyridine, dimethylaminobenzene, 1,4-diaminobenzene, 2,4-diaminopyridine, 4-cyanopyridine, benzamide, benzonitrile, phenetole, o, m, p-dimethylbenzene, 1-chloronaphthalene, 2,5-dichloronaphthalene, 1-fluoroanthracene, 2-methylphenanthrene, diphenylmethane, 4-phenyl-2-methylpyridine, xylyl methyl benzene, 2(bisphenyl) propane, phenoxy benzene, N,N-diethylaminobenzene, 4-(N-phenylamino) pyridine, N-pentylaminobenzene, m-phenylenediamine, 3-amido-pyridine, 1-methyl-3-ethylbenzene, o-, m- and p-chloroaniline, o-, m- and p-chlorobenzonitrile, 2-chloro-4-cyanopyridine, p-methoxybenzamide; cyclohexylbenzene, 4-cyclopentylpyridine, 4-(N-methyl-N-phenyl) amino-pyridine, 3-hydroxy-pyridine, 1-hydroxy-3-chlorobenzene, 3-methoxy-quinoline, 5-cyanoisoquinoline, 4,4'-dicyanodiphenyl, 4-hydroxy-4'-fluorobiphenyl, 1,4-dichloroanthracene, 2,7-dihydroxy-phenanthrene, 1-chloro-5-amidonaphthalene, 5-phenoxy-isoquinoline, 3-chloro-4-fluoroquinoline, 2-pentoxy-7-hydroxyphenanthrene, 1-(2,3-dimethylphenyl) naphthalene, 1,4-dichloronaphthalene, methylisopropyl phenanthrene, 9,10-dichloroanthracene, anthradiamine, dihydroanthracene, 2,3-dimethylanthracene, 9-ethylanthracene, aminoquinoline, aminophenylmethylquinoline, benzoquinoline, chloroquinoline, dimethylquinoline, quinolinol, methoxyquinoline, α-methylquinoline, cyanoquinoline, 1-benzyl-N-methylisoquinoline, N-methyl pyridine, 3-benzylpyridine, 3,5-dimethylpyridine, 4-hydroxypyridine, 3-methyl-5-ethylpyridine, 4-propyl-pyridine, α-naphthylamine, 1-benzyl-naphthalene, 1- or 2-chloronaphthalene, any of the naphthalene diamines, naphthalene diols, dichloronaphthalenes, and dimethylnaphthalenes, 1-ethoxynaphthalene, 1- or 2-fluoronaphthalene, iopropylmethylnaphthalene, 1- or 2-ethylnaphthalene, 1-methylisopropylnaphthalene, 1-phenylnaphthalene, naphthamide and the like as well as any other compounds which come within the definition and formula set out hereinbefore which will occur to those skilled in the art.

Benzene and pyridine are also preferred aromatic compounds of the present invention when the production of aniline and 2-aminopyridine are the preferred objective. Aniline as well as toluene are likewise preferred aromatic compounds.

The aromatic amines prepared by the process of this invention are useful in any application in which prior art aromatic amines have been employed such as, for example, in the preparation of isocyanates used to react with polyols in the production of urethanes.

The invention is further illustrated but is not intended to be limited by the following examples in which all parts and percentages are by weight unless otherwise specified.

Preparation of Cataloreactant A

A. Salt Precipitation

Cataloreactant A was prepared by stirring 150 parts of nickelous nitrate and 60 parts of zirconyl nitrate in 3 liters of deionized-distilled water until they dissolve. A solution of 60 parts of sodium hydroxide pellets in 6 liters of deionized-distilled water was added to the metal salt solution in one liter portions with stirring until all 6 liters had been added. The resulting gel was filtered, washed three times by mixing thoroughly with 40 liters of deionized-distilled water and finally filtered to yield a hard cake which was dried in an oven at 100° to 110° C. to yield hard, glassy granules.

B. Conditioning

Approximately 250 parts of the hard glassy granules prepared in A were heated in an 18 × 1¼ inches Pyrex tube beginning at a temperature of 25° C. and increasing to 300° C over 1 hour at atmospheric pressure starting with a stream of 40 cc./min. of hydrogen and 360 cc./min. of nitrogen. As the temperature increased the percentage of $H_2$ in the stream was increased to 90 percent at 300° C. while the total gas flow was maintained at 400 cc./min. The temperature was then increased sharply to 380° C. while the flow of 90 percent $H_2$ and 10 percent $N_2$ gas was increased to 750 cc./min. These conditions were maintained for 5 hours after which the tube was cooled to 100° C. under 130 cc./min. $N_2$ and oxidized with 3 percent $O_2$ (130 cc./min. total flow) at 100° C. for 16 hours then 5 percent $O_2$ at 100° C. for 1 hour then 7 percent for 1 hour at 100° C. with the same total gas flow. About 150 parts of hard glassy conditioned cataloreactant granules were obtained.

Preparation of Cataloreactant B

A. Salt Precipitation

Cataloreactant B was prepared in the same manner as cataloreactant A except that 3.0 parts of lanthanum nitrate were added simultaneously with the 150 parts of nickelous nitrate and 60 parts of zirconyl nitrate to 3 liters of deionized, distilled water.

B. Conditioning

The conditioning of cataloreactant B was the same in every respect as the conditioning of cataloreactant A.

Cataloreactants C–L in Table I were prepared in the same manner except that the appropriate amount of nickel, zirconyl and dopant metal nitrate were used to yield the proportions set forth for the cataloreactants in Table I.

EXAMPLES 1–12

About 60 grams of cataloreactant were loaded into a 20 × ½ inches stainless steel reactor tube which was then attached to feed and exit lines. The reactor was heated to a reaction temperature of about 350° C. and ammonia and benzene at a mole ratio of $NH_3/C_6H_6$ of 3 were fed into the reactor at a rate of about 3.0 to 3.5 g./minute. The pressure in the reactor was maintained at 4400 to 4500 psig. Because the feed was premixed, only one pump was required, and the feed composition remained constant. Samples were collected every 10–15 minutes for a total of 120 minutes and analyzed by gas chromatography. The peak weight percent conversion of benzene to aniline over the total 120-minute period for cataloreactants A–L is set forth in the following table:

TABLE I

| Example No. | Cataloreactant | Peak Weight Percent Conversion of Benzene to Aniline |
|---|---|---|
| 1 | A. Ni/0.3Zr | 5.5 |
| 2 | B. Ni/0.3Zr/.014La | 9.4 |
| 3 | C. Ni/.3Zr/.015Y | 9.5 |
| 4 | D. Ni/.3Zr/.015Ho | 9.0 |
| 5 | E. Ni/.3Zr/.015Dy | 8.2 |
| 6 | F. Ni/.3Zr/.015Yb | 10.5 |
| 7 | G. Ni/.3Zr/.015Sm | 9.5 |
| 8 | H. Ni/.3Zr/.015Pr | 10.2 |

TABLE I-continued

| Example No. | Cataloreactant | Peak Weight Percent Conversion of Benzene to Aniline |
|---|---|---|
| 9 | I. Ni/.2Zr/.014La | 9.0 |
| 10 | J. Ni/.3Zr/0.02Y | 9.2 |
| 11 | K. Ni/.2Zr/.028La | 7.9 |
| 12 | L. Ni/.3Zr/.042La | 7.5 |

EXAMPLES 13–17

A. Preparation of Cataloreactant

The cataloreactant was prepared and conditioned as described in Example 2 except that 1.5 parts of lanthanum nitrate were added to the nickelous and zirconyl nitrates.

B. Preparation of Aniline 241 gm. of the Ni/.3Zr/.007La cataloreactant of A were loaded into a 1 × 36 inches stainless steel reactor. The reactor was attached to feed and exit lines and heated to 350° C. The cataloreactant was purged with ammonia for 5 minutes after which the exit valve was closed and the reactor pressured to 125 to 140 psig with ammonia. After 10 more minutes the feed pump was started and ammonia and benzene at a molar ratio of 3 were introduced into the reactor at a rate of 7.8 to 8.5 grams of the mixture of ammonia and benzene. When the pressure reached 7000 psig the reaction was carried on for about 90 minutes. Samples were taken every 10 minutes during this 90 minute time period and analyzed by gas chromatography. At the end of the run the feed pump was stopped, and the reactor slowly vented to 500 psig.

In order to regenerate the cataloreactant, the reactor was flushed with nitrogen for 10 minutes at 500 psig after which a feed containing 1.3 percent oxygen in nitrogen was added to the reactor at about 0.5 to 1.0 standard cubic feet per minute until the uptake of oxygen ceased. The reactor was then purged with nitrogen and the next run started with the regenerated cataloreactant. The amount of aniline obtained in Example 13 for each 10 minutes of the 90-minute run is outlined in Table 2. A resume of runs 13 through 17 is outlined in Table 3.

TABLE 2

| Sample No. | Time | Weight of Benzene and Aniline recovered in Grams | Weight Percent conversion of Benzene to Aniline |
|---|---|---|---|
| 1 | 10 | 37.17 | 7.3 |
| 2 | 20 | 37.81 | 11.4 |
| 3 | 30 | 41.91 | 13.75 |
| 4 | 40 | 47.14 | 11.98 |
| 5 | 50 | 36.77 | 12.98 |
| 6 | 60 | 37.35 | 12.22 |
| 7 | 70 | 40.23 | 11.1 |
| 8 | 80 | 41.75 | 8.2 |
| 9 | 90 | 39.12 | 10.5 |

TABLE 3

| Example | Weight percent conversion of Benzene to Aniline |
|---|---|
| 13 | 11.1 |
| 14 | 12.2 |
| 15 | 12.6 |
| 16 | 12.4 |
| 17 | 12.8 |

It is to be understood that any of the components and conditions mentioned as suitable herein can be substituted for its counterpart in the foregoing examples and that although the invention has been described in considerable detail in the foregoing, such detail is solely for the purpose of illustration. Variations can be made in the invention by those skilled in the art without departing from the spirit and scope of the invention except as set forth in the claims.

What is claimed is:

1. In a process of the present invention an aromatic compound selected from anthracene; phenanthrene; quinoline; isoquinoline and compounds having the formula $(X)_m(Y)_n$ wherein X is benzene or pyridine, $m$ is 1 or 2, $n$ is 0, 1 or 2, and Y is alkyl having one to six carbon atoms, halogen, nitrile, hydroxy, $CONH_2$, alkoxy having one to six carbon atoms, aryloxy, amino and aralkyl, with the proviso that when Y is aryloxy, a secondary or tertiary arylamine or an aralkyl, $n$ is 1 and when $n$ is 2, the substituents Y may be the same or different, is aminated by reacting ammonia with said aromatic compound at a temperature of from about 150° C. to about 500° C. and at a pressure of from about 10 to 1000 atmospheres, in the presence of a conditioned $Ni/NiO/ZrO_2$ cataloreactant with a mole ratio of nickel to nickel oxide of 0.001 to 10, the improvement which comprises carrying out the reaction in intimate molecular contact with said conditioned cataloreactant containing a molar ratio of 0.0001 to 0.05 of a dopant to total nickel, wherein said dopant is selected from an oxide of lanthanum, samarium, holmium, europium, erbium, praseodymium, neodymium, tertium, ytterbium, dysprosium, yttrium and mixtures thereof.

2. The improvement of claim 1 wherein the mole ratio of total nickel to zirconium oxide expressed as total nickel to zirconium is 0.1 to 100.

3. The improvement of claim 1 wherein the mole ratio of ammonia/aromatic compound is 0.1 to 20.

4. The improvement of claim 1 wherein the cataloreactant-dopant is treated with ammonia prior to introduction to the aromatic compound and ammonia.

5. The improvement of claim 1 wherein the aromatic compound is benzene.

6. The improvement of claim 1 wherein the aromatic compound is pyridine.

7. The improvement of claim 1 wherein the aromatic compound is aniline.

8. The improvement of claim 1 wherein the aromatic compound is toluene.

* * * * *

UNITED STATES PATENT OFFICE
CERTIFICATE OF CORRECTION

PATENT NO. : 4,031,106
DATED : JUNE 21, 1977
INVENTOR(S) : THOMAS WAYNE DEL PESCO

It is certified that error appears in the above-identified patent and that said Letters Patent are hereby corrected as shown below:

Column 10, line 42, "tertium" should be -- terbium --.

Signed and Sealed this

First Day of November 1977

[SEAL]

Attest:

RUTH C. MASON
*Attesting Officer*

LUTRELLE F. PARKER
*Acting Commissioner of Patents and Trademarks*